US00PP27733P2

(12) United States Plant Patent
Williams

(10) Patent No.: US PP27,733 P2
(45) Date of Patent: Feb. 28, 2017

(54) ***COLOCASIA* PLANT NAMED 'PAINTED BLACK GECKO'**

(50) Latin Name: ***Colocasia* hybrid**
Varietal Denomination: Painted Black Gecko

(71) Applicant: Brian Paul Williams, Louisville, KY (US)

(72) Inventor: Brian Paul Williams, Louisville, KY (US)

(73) Assignee: BRIAN'S BOTANICALS, Louisville, KY (US)

( * ) Notice: Subject to any disclaimer, the term of this patent is extended or adjusted under 35 U.S.C. 154(b) by 95 days.

(21) Appl. No.: 14/544,742

(22) Filed: Feb. 10, 2015

(51) Int. Cl.
*A01H 5/12* (2006.01)

(52) U.S. Cl.
USPC ..... Plt./373

(58) Field of Classification Search
USPC ..... Plt./373
See application file for complete search history.

(56) References Cited

PUBLICATIONS

Florida Hill Nursery. *Colocasia* "Painted Black Gecko" Elephant ear Plant, retrieved on Jul. 7, 2016, retrieved from the Internet at <http://www.floridahillnursery.com/colocasia-elephant-ear-plant-c-2/colocasia-painted-black-gecko-elephant-ear-plant-p-490> 2 pp.*

* cited by examiner

*Primary Examiner* — June Hwu
(74) *Attorney, Agent, or Firm* — Penny J. Aguirre

(57) ABSTRACT

A new cultivar of *Colocasia* plant named 'Painted Black Gecko', that is characterized by its clump forming, medium-sized plant habit growing 1.2 to 1.5 m in height, its leaves that are very dark purple-black in color with a blue metallic sheen, its leaves with lower surfaces that are dark maroon in color, its petioles that are dark purple-black in color, its healthy root system that is that is resilient to cold in U.S.D.A. Zone 7, and its production of tubers as it ages.

2 Drawing Sheets

Botanical classification: *Colocasia* hybrid.
Cultivar designation: 'Painted Black Gecko'.

BACKGROUND OF THE INVENTION

The present invention, *Colocasia* 'Painted Black Gecko', relates to a new and distinct interspecific hybrid of *Colocasia*, hereinafter referred to by its cultivar name, 'Painted Black Gecko'. 'Painted Black Gecko' is a new tropical plant used as a landscape and container plant in tropical and subtropical areas.

The new cultivar was derived from a controlled breeding program conducted by the Inventor at his nursery in Louisville, Ky. The overall purpose of the breeding program is to make selections of *Colocasia* plants with unique foliage coloration in a variety of sizes and that exhibit leaf sheen. 'Painted Black Gecko' arose from a cross make in June of 2011 between unnamed proprietary *Colocasia* hybrid plants (not patented) from the Inventor's breeding program as both the female and male parents. 'Painted Black Gecko' was selected as a single unique plant in June of 2013 from amongst the seedlings derived from the above cross.

Asexual propagation of the new cultivar was first accomplished by in vitro propagation, specifically meristematic cell tissue culture, under the direction of the Inventor in Eustis, Fla. in February of 2014. Asexual propagation by in vitro propagation has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Painted Black Gecko' as a new and unique cultivar of *Colocasia*.

1. 'Painted Black Gecko' exhibits a clump forming, medium-sized plant habit growing 1.2 to 1.5 m in height.
2. 'Painted Black Gecko' exhibits leaves with upper surfaces that are very dark purple-black in color with a blue metallic sheen.
3. 'Painted Black Gecko' exhibits leaves with lower surfaces that are dark maroon in color.
4. 'Painted Black Gecko' exhibits petioles that are dark purple-black in color.
5. 'Painted Black Gecko' exhibits a healthy root system that is resilient to cold in U.S.D.A. zone 7.
6. 'Painted Black Gecko' can produce large tubers with age.

The female parent of 'Painted Black Gecko', differs from 'Painted Black Gecko' in being taller in height, in having a spreading plant habit, in having leaves that are dark brown in color with a clear sheen, and in having petioles that are brown-black in color. The male parent of 'Painted Black Gecko', differs from 'Painted Black Gecko' in having leaves that are dark blue-green in color with a dull surface, in having petioles that are more purple in color, and in having leaf lower surfaces that are gray-green in color. 'Painted Black Gecko' can be most closely compared to the *Colocasia* cultivars 'Black Magic' (not patented) and 'Mojito' (U.S. Plant Pat. No. 21,995). 'Black Magic' differs from 'Painted Black Gecko' in having leaves with the upper surface lacking a blue sheen and in having leaf lower surfaces that are gray in color. 'Mojito' differs from 'Painted Black Gecko' in having petioles with dark streaks and in having leaves that are lime green in color with black variegation.

BRIEF DESCRIPTION OF THE DRAWINGS

The accompanying colored photographs illustrate the overall appearance and distinct characteristics of the new *Colocasia*, 'Painted Black Gecko'. The photographs were taken of 2 year-old plants as grown outdoors, in full sun, under 2 mm poly in Louisville, Ky.

The photograph in FIG. 1 provides an overall view of the mature foliage and plant habit of 'Painted Black Gecko'.

Figure 1:
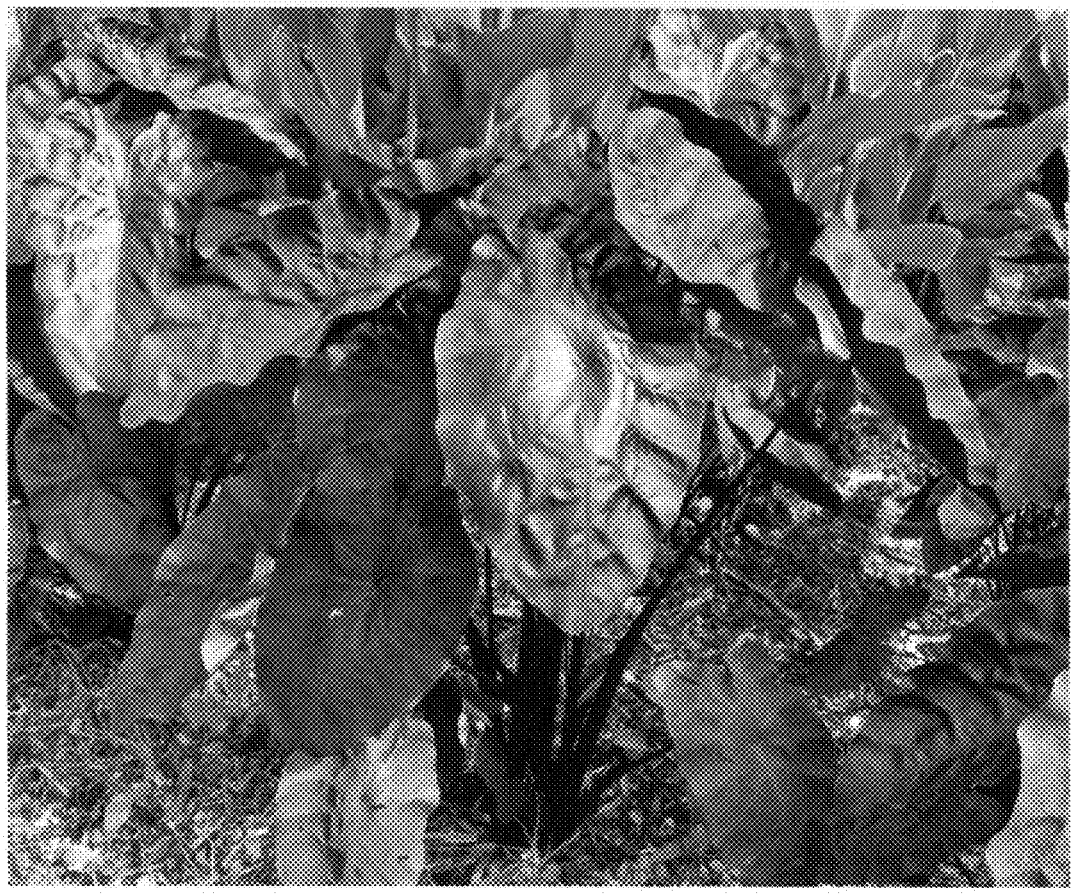
Figure 2:
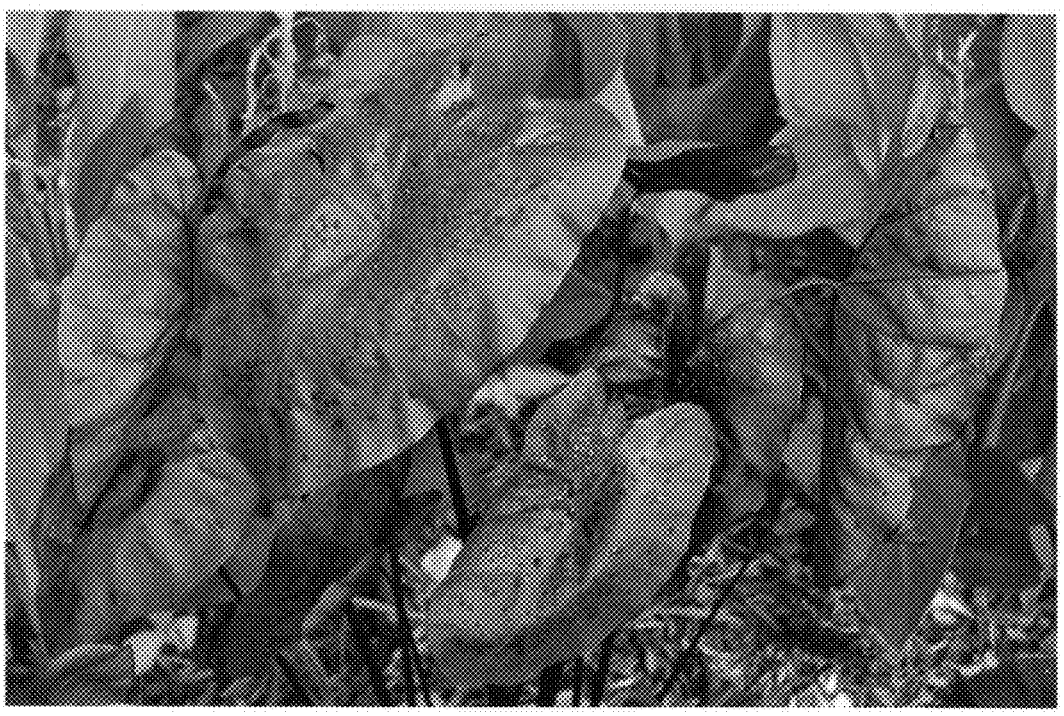

The photograph in FIG. 2 provides a close-up view of the upper leaf surface in the center and the lower leaf surface on the left and right of 'Painted Black Gecko'.

The colors in the photographs are as close as possible with the digital photography techniques available, the color values cited in the detailed botanical description accurately describe the colors of the new *Colocasia*.

DETAILED BOTANICAL DESCRIPTION OF THE PLANT

The following is a detailed description of three year-old plants of the new cultivar plants as grown outdoors, in full sun, under 2 mm poly in Louisville, Kentucky. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—August to September in Kentucky.

*Plant type.*—Tropical perennial herb.

*Plant habit.*—Upright, stemless, clump forming.

*Height and spread.*—Reaches 1.2 to 1.5 m in height and 0.9 to 1.2 m in width.

*Cold hardiness.*—At least to U.S.D.A. Zone 7a.

*Diseases and pests.*—No particular resistance and susceptibility to diseases or pests has been observed.

*Roots.*—Fleshy.

*Propagation type.*—In vitro propagation.

*Growth rate.*—Vigorous.

*Stem description.*—Stemless, can produce large corms with age.

*Corm description.*—Fleshy, globose oval in shape, an average of 7 cm in diameter, color; a blend between 164C and 165A to 165B, rough, exfoliating surface.

Foliage description:

*Leaf shape.*—Oval.

*Leaf division.*—Single.

*Leaf base.*—Cordate.

*Leaf apex.*—Broadly acute.

*Leaf venation.*—Pinnate, color matches leaf coloration.

*Leaf margins.*—Entire and undulate.

*Leaf attachment.*—Petiolate.

*Leaf arrangement.*—Emerge from tuber.

*Leaf surface.*—Upper surface and lower surface; coriaceous and glabrous, upper surface develops a metallic sheen.

*Leaf orientation.*—Held horizontal to downward.

*Leaf color.*—Young foliage: upper surface; a blend between N186A and N189A and lower surface; N77D, mature foliage upper surface; N186A suffused with a color closest to 102D, mature foliage lower surface: N77C.

*Leaf size.*—An average of 40 cm in length and 22 cm in width.

*Petioles.*—Held erect to semi-erect, an average of 38 cm in length and 4 mm in distal diameter and 15 mm in proximal diameter, glaucescent surface, color; 144D lightly suffused with 183A, tuber-like trunk; formed at the base of the petioles with age, about 10 cm in length and 15 cm in width on a 2 year-old plant, comprised of petiole scales, surface is rough and paper-like, color is a blend of N199B and N199D.

Inflorescence description:

*Inflorescence type.*—Spadix surrounded by a spathe, male portion held above female portion, only female flowers are developed.

*Inflorescence size.*—An average of 16 cm in length and 1.3 cm in width.

*Inflorescence bud.*—Linear to slightly narrow lanceolate in shape, an average of 13 cm in length and 3 cm in width.

*Flower fragrance.*—None.

*Lastingness of inflorescence.*—Inflorescence blooms intermittently during the bloom period, individual flowers last about 2 to 3 weeks.

*Inflorescence/flower quantity.*—An average of 80 female flowers sessile to spadix, sessile male flowers are undeveloped.

*Spathe.*—Hooded, bract, subtending spadix, an average of 15.5 cm in length and 2.9 cm in width, entire margin, bottom portion; flattened rotund shape, an average of 2.8 cm in length and 3.1 cm in width, apex fused to upper portion, upper portion (hood); elongated oval in shape, an average of 12 cm in length and 3 cm in width, acute apex, upper and lower portion inner and outer surface; coriaceous, smooth, and glabrous, color; lower portion outer surface a blend of N187A and 202A and inner surface; a blend of 145C and 193A suffused with N187A, upper portion inner surface; 145B to 145C and outer surface a mix of 145A to 145B and 150C lightly suffused with N187A, color fades to 164C.

*Spadix.*—Male portion above female zone, upright linear to slightly narrow oblanceolate in shape (phallus like), apex narrowly pointed, an average of 9.4 cm in length, male portion; an average of 7.6 cm in length and 5.5 mm in width, female portion; an average of 2 cm in length and 8.5 cm in width, color; male portion NN155A suffused with a blend of 77B and N187B and female portion a mix between 145A, NN155A, and N187A.

*Peduncle.*—Grows from base of plant, rotund to rounded in shape, an average of 17.5 cm in length and 6.5 mm in diameter, durable and strong, a blend of N187A and 102A in color, glabrous and smooth surface.

Reproductive organs:

*Gynoecium.*—1 pistil with sessile, discoid stigmas; N92A in color, monocarpous ovary is full of many minute ovules; oval in shape and translucent in color.

*Androcoecium.*—Undeveloped.

*Fruit and seed.*—Sterile.

It is claimed:

1. A new and distinct cultivar of *Colocasia* plant named 'Painted Black Gecko' as herein illustrated and described.

* * * * *